United States Patent [19]

Ganti

[11] 4,451,470

[45] May 29, 1984

[54] ANALGESIC, ANTAGONIST, AND/OR ANORECTIC 14-FLUOROMORPHINANS

[75] Inventor: Venkat Ganti, Wilmington, Del.

[73] Assignee: E. I. Du Pont de Nemours and Company, Wilmington, Del.

[21] Appl. No.: 395,597

[22] Filed: Jul. 6, 1982

[51] Int. Cl.$^3$ .................. A61K 31/485; C07D 489/06
[52] U.S. Cl. ...................................... 424/260; 546/15; 546/44; 546/45
[58] Field of Search .................. 546/44, 45, 46, 74, 546/15; 424/260

[56] References Cited

U.S. PATENT DOCUMENTS

| | | | |
|---|---|---|---|
| 2,797,223 | 6/1957 | Conroy | 546/45 |
| 3,137,701 | 6/1964 | Ayer | 546/46 |
| 3,332,950 | 7/1967 | Blumberg et al. | 546/45 |
| 3,914,265 | 10/1975 | Middleton | 260/397.3 |
| 4,236,008 | 11/1980 | Henderson | 546/46 |
| 4,241,065 | 12/1980 | Boswell et al. | 424/260 |

FOREIGN PATENT DOCUMENTS 913077 10/1982 Canada.

OTHER PUBLICATIONS

Middleton, J. Org. Chem., 40 (1975), pp. 574–578.
Zimmerman et al., Ann. Repts. Med. Chem., 17 (1982), p. 24.
Osei-Gyimah et al., J. Med. Chem., 24 (1981), pp. 212–214.
Bognar et al., Acta Chim. Acad. Sci. Hung., 67 (1971), 63–69.

*Primary Examiner*—Donald G. Daus
*Assistant Examiner*—Diana G. Rivers

[57] ABSTRACT

14-Fluoromorphinans such as 17-cyclopropylmethyl-4,5-epoxy-14-fluoro-3-hydroxymorphinan-6-one are useful as analgesics, narcotic antagonists, and/or anorexigenic agents.

8 Claims, No Drawings

ANALGESIC, ANTAGONIST, AND/OR ANORECTIC 14-FLUOROMORPHINANS

BACKGROUND OF THE INVENTION

1. Field of Invention:

This invention relates to 14-fluoromorphinans, their preparation, pharmaceutical compositions containing them, and methods of using them to treat pain, narcotic addiction and/or obesity in mammals.

2. Prior Art:

Morphine and codeine analgesics are addicting. Considerable effort has been made for many years to find derivatives that are not addicting and still have analgesic effects. Compounds which are narcotic antagonists such as naloxone, naltrexone and nalorphine are also useful in medicine, e.g., in the treatment of addicts.

Fluorine derivatives of codeine in which the 6-hydroxy group has been replaced by fluorine are known [Ayer, U.S. Pat. No. 3,137,701; Bognar et al., *Acta. Chim. Acad. Sci. Hung.*, 67, 63–69 (1971)]

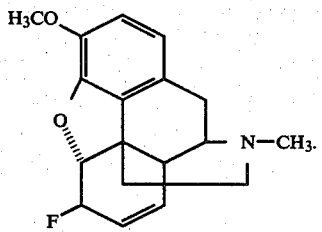

Fluorine derivatives of hydrocodone and oxycodone with one or two fluorines in the 6-position are also known (Boswell et al., U.S. Pat. No. 4,241,065)

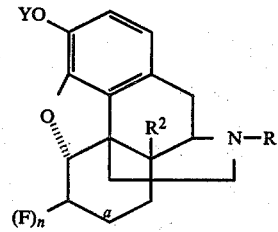

wherein $R^2$=H, OH, or $C_{1-4}$ alkanoate.

Henderson, U.S. Pat. No. 4,236,008, describes a process for converting 6-keto morphinans to 6,6-difluorides and to 6-fluoro-$\Delta^{6,7}$-derivatives. The 14-substituent, $R^2$, can be H, F, OH, or $C_{1-4}$ alkanoyl oxy. Examples 4 and 5 describe the preparation of compounds where $R^2$ is F, F being introduced by reaction of the compounds where $R^2$ is OH with diethylaminosulfur trifluoride (DAST).

W. J. Middleton, *J. Org. Chem.*, 40, 574 (1975), describes conversion of alcohols to fluorides with DAST. U.S. Pat. No. 3,914,265 to Middleton claims this conversion process.

SUMMARY OF THE INVENTION

According to the present invention there is provided a compound having the formula:

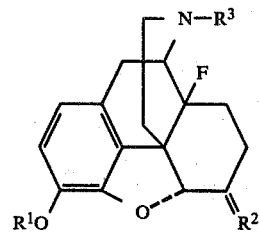

wherein
$R^1$ is —H, —$CH_3$ or

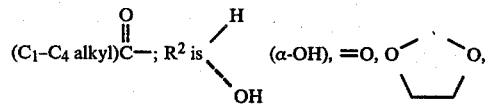

or (O—$C_1$ to $C_6$ alkyl)$_2$; and
$R^3$ is $C_1$–$C_5$ alkyl,

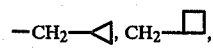

allyl or 3,3-dimethylallyl;
or a pharmaceutically suitable salt thereof.

Pharmaceutically suitable salts are those made with physiologically acceptable acids that are well known in the art. Such salts include hydrochloride, sulfate, phosphate, nitrate, citrate, maleate, and the like.

Preferred compounds of the invention are those of Formula I where
$R^1$ is —H, —$CH_3$, or acetyl; and/or
$R^3$ is cyclopropylmethyl or cyclobutylmethyl.

Specifically preferred compounds of Formula I are those in which:

(1) $R^1$ is H; $R^2$ is=O and $R^3$ is cyclopropylmethyl; and
(2) $R^1$ is H; $R^2$ is

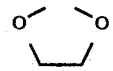

and $R^3$ is cyclopropylmethyl.

There is also provided a process for preparing the aforesaid compounds which comprises:

(a) contacting and reacting a dialkylaminosulfur trifluoride with a compound of the formula:

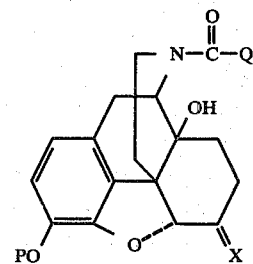

wherein
P is alkyl or

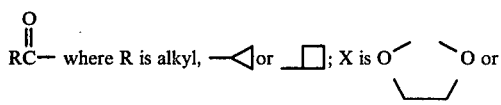 where R is alkyl, —◁ or —□; X is O—O or (OC₁ to C₆ alkyl)₂; and Q is alkyl, —◁, —□, or alkoxy;

(b) reducing 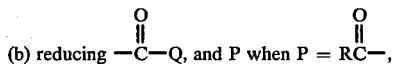

to —CH₂Q (or —CH₃ when Q in 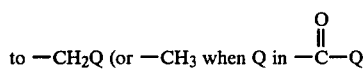

is alkoxy) and H respectively;

(c) optionally deketalizing to provide a compound in which X is changed to =O;

(d) optionally reducing the compound from (c) where X is =O to a compound in which X is changed to

(the 6α-hydroxy derivative); and (e) optionally dealkylating the product of (b), (c), or (d) when P is alkyl to obtain a compound in which $R^1$ is H.

Also provided are pharmaceutical compositions containing at least one of the aforesaid compounds and methods of using them to treat addiction, obesity and/or alleviate pain in mammals.

DETAILED DESCRIPTION OF THE INVENTION

Compounds of Formula I can be prepared by reacting a 4,5-epoxy-14-hydroxymorphinan with a dialkylaminosulfur trifluoride, (DAST), fluorinating agent (W. J. Middleton, E. M. Bingham, *Org. Syn.*, 57, p. 50, 72 (1978)). In order to obtain reaction with the fluorinating agent exclusively at the 14-position, the other reactive groups have to be protected. The hydroxyl group in the 3-position is converted to a carboxylic acid ester, or an alkyl ether. The 6-keto group is converted to a ketal. For the introduction of the alkyl group at the 17-position, one uses an appropriate carboxamide derivative, which on subsequent reduction will result in the formation of the alkyl group. The reduction of the 6-keto group to the 6-α-hydroxyl group can be carried out by reducing agents such as lithium tri(tertiarybutoxy)aluminum hydride.

These reactions are shown in the following schemes:

Scheme 1

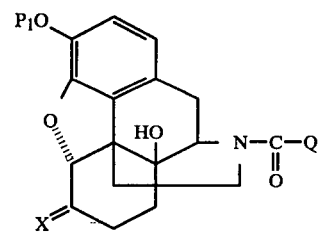

P₁ = alkyl.
X = protective group for the keto functionality such as an ethylene ketal, or dialkyl ketal.
Q = alkyl, cyclopropyl, cyclobutyl, or alkoxy.

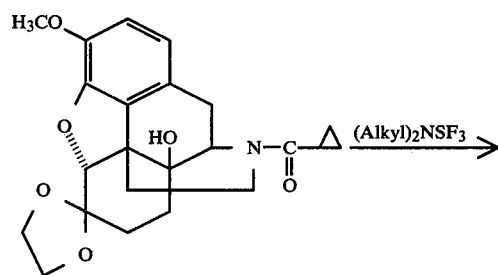

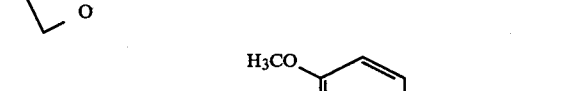

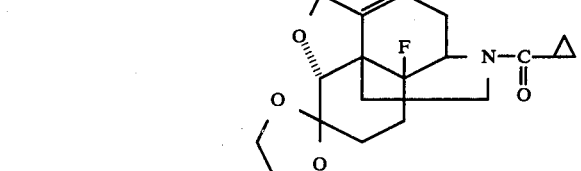

LiAlH₄

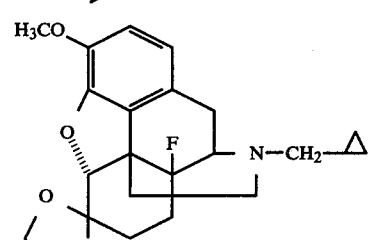

H⊕

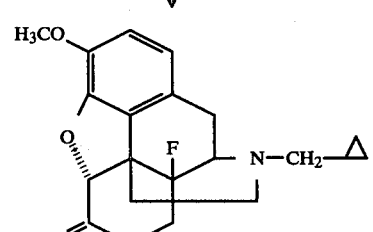

3-O—Dealkylation

-continued
Scheme 1

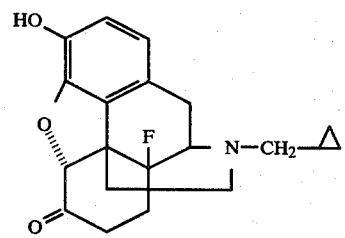

Scheme 2

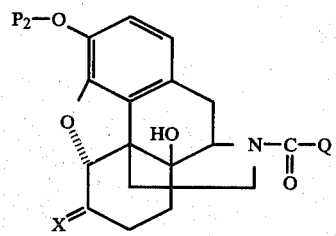

P₂ is an acyl protective group for the 3-hydroxyl group;
Q and X have the same definitions as in Scheme 1.

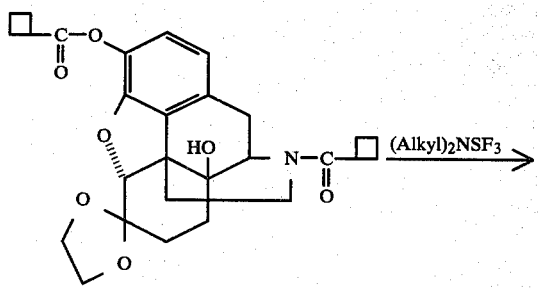

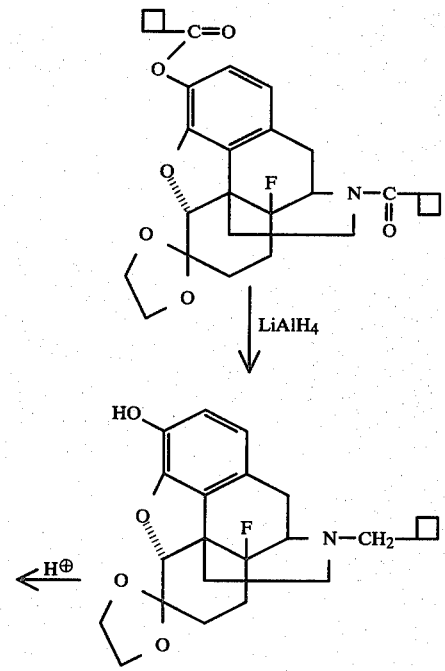

-continued
Scheme 2

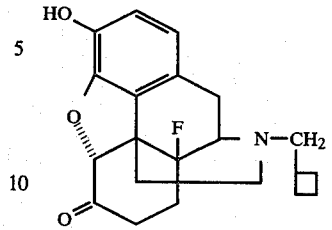

reduction with lithium tri-
(tertiarybutoxy)aluminum
hydride

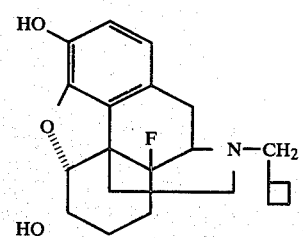

To prepare compounds in which R₃ is allyl, or 3,3-dimethylallyl, one converts 14-fluorodihydromorphinone (preparation described in Example 7) to 14-fluorodihydronormorphinone according to the procedures described by von Braun, Ber., 59, 1081 (1926). Alkylation of this intermediate with allyl bromide or with 1-bromo-3-methyl-2-butene yields the N-allyl, and N-(3,3-dimethylallyl)-14-fluoro derivatives, respectively; the procedures are analogous to those of Brit. Pat. No. 939,287.

The acetylation of 3-hydroxy-14-fluoro compounds to give the 3-acetoxy compounds is possible by adapting the procedure described by L. H. Welsh [*J. Org. Chem.*, 19, 1409 (1954)], using acetic anhydride and aqueous sodium bicarbonate.

The invention can be further understood by the following examples in which temperatures are in Celsius and parts and percentages are by weight, except that ratios of solvent mixtures are by volume.

EXAMPLE 1 a. Preparation of Intermediate
17'-(Cyclopropylcarbonyl)-4',5'-epoxy-14'-fluoro-3'-methoxyspiro[1,3-dioxolane-2,6'-morphinan]

A solution of the amide, 17'-(cyclopropylcarbonyl)-4',5'-epoxy-3'-methoxyspiro[1,3-dioxolane-2,6'-morphinan]-14-ol (Canadian Pat. No. 913077, October, 1972) (8 gm, ~0.02 moles) in 80 ml of methylene chloride was added dropwise to a solution of diethylaminosulfurtrifluoride (4 gm in 75 ml of methylene chloride) maintained at −78° C., during a period of ten minutes. The temperature was allowed to rise gradually, and the reaction allowed to proceed for a period of approximately 18 hours. The reaction mixture then was poured gradually into a stirred solution of aqueous saturated potassium bicarbonate, containing ice chips. The methylene chloride layer was separated, washed with water, filtered through a fluted paper, and the solvent removed by evaporation under reduced pressure. Residue was recrystallized from methanol to yield 6.4 gms of the title product, m.p. 191°–193°.

Mass spectrum: Calcd. for $C_{23}H_{26}NO_5F$, 415; found, 415.

b.
17'-(Cyclopropylmethyl-4',5'-epoxy-14'-fluoro-3'-methoxyspiro[1,3-dioxolane-2,6'-morphinan]

To a solution of lithium aluminum hydride (1.75 g) in tetrahydrofuran (THF) (100 ml), the above obtained 14'-fluoro-17'-cyclopropylcarbonyl compound from several preparations (7.5 gm in 200 ml tetrahydrofuran) was added gradually. After all the amide solution was added, the reaction mixture was heated at reflux for 3.5 hours, cooled, and the excess lithium aluminum hydride decomposed by the addition of 20 ml ethyl acetate, followed by 50 ml water. The inorganic salts were removed by filtration, and the filter cake washed with tetrahydrofuran. Evaporation of the aqueous tetrahydrofuran filtrate yielded a residue which was washed well with water and air dried to yield 6.8 g of solids. Recrystallization from methanol provided 5.2 g of the title product which melted at 163°–164°.

Mass Spectrum: Calcd. for $C_{23}H_{28}NO_4F$, 401; found, 401.

EXAMPLE 2

17-(Cyclopropylmethyl)-4,5-epoxy-14-fluoro-3-methoxymorphinan-6-one

A mixture of 75 ml of aqueous hydrochloric acid (0.6 N) and 4.9 g of the ketal from Example 1 was heated to reflux for 6 hours, cooled to 25° and adjusted to pH 9.4 with aqueous $NH_3$. The precipitate was filtered off and washed with water. This compound melted at 99°–102°.

Mass Spectrum: Calcd. for $C_{21}H_{24}FNO_3$, 357; found, 357.

EXAMPLE 3

17-(Cyclopropylmethyl)-4,5-epoxy-14-fluoro-3-hydroxymorphinan-6-one

Boron tribromide (2.5 ml) was dissolved in chloroform (75 ml), and chilled to 20°–25°. A solution of 17-(cyclopropylmethyl)-4,5-epoxy-14-fluoro-3-methoxymorphinan-6-one (1.25 g in 25 ml chloroform) was added and the mixture stirred at that temperature for one-half hour. The reaction mixture was then dumped with good stirring onto 80 g of ice containing 5 ml of concentrated ammonium hydroxide at approximately pH 9.2. The chloroform solution was vigorously shaken, washed with water, then extracted with 5% sodium hydroxide solution. The alkali extract was then separated, acidified, and the liberated phenolic compound taken up in chloroform, washed, and dried over molecular sieve. The dried solvent extract was evaporated, and the crude product column chromatographed using silica gel and, as eluant, a solvent mixture comprising 95% chloroform and 5% ethanol. The purified product was crystallized from ethanol, m.p. 188°–190°.

Mass spectrum: Calcd. for $C_{20}H_{22}NO_3F$, 343; found, 343.

EXAMPLE 4 a.
17'-(Cyclobutylcarbonyl)-3'-(cyclobutylcarbonyloxy)-4',5'-epoxyspiro[1,3-dioxolane-2,6'-morphinan]-14'-ol To a stirred suspension of 4',5'-epoxyspiro[1,3-dioxolane-2,6'-morphinan]-3'-14'-diol (U.S. Pat. No. 3,332,950, July 25, 1967) (3.31 g, 0.01 mole) in 100 ml of chloroform, triethylamine (7 ml; excess) was added, followed by the addition of cyclobutane carboxylic acid chloride (2.4 g, 0.02 mole) at room temperature. After one hour, the reaction mixture was diluted with 100 ml of chloroform and washed with 3% ice-cold hydrochloric acid, then water, saturated sodium bicarbonate, and water. The resulting precipitate was filtered through a fluted filter and dried over molecular sieves. The drying agent was filtered off, and the chloroform evaporated to yield a gummy residue which was used for the next step.

b.
17'-(Cyclobutylcarbonyl)-3'-(cyclobutylcarbonyloxy)-4',5'-epoxy-14'-fluorospiro[1,3-dioxolane-2,6'-morphinan]

A solution of diethylaminosulfurtrifluoride (2 ml) in methylene chloride (50 ml) was cooled to −78°. A solution of the above-obtained amide ester (step a) in methylene chloride (50 ml) was then added dropwise to the chilled reagent. The reaction mixture was allowed to stand overnight and to warm to room temperature. The mixture was poured into a stirred saturated solution of potassium bicarbonate containing chips of ice. The methylene chloride solution was washed with water and dried over molecular sieves. The product obtained by the evaporation of the solvent was a gum, which solidified on trituration with hexane. Thin layer chromatographic examination (95 chloroform/5 ethanol) showed it to be mainly one component. Mass spectral examination for $C_{28}H_{32}NO_6F$ (497); found, 497. This derivative was used as such for the reduction in the next step.

c.
17'-(Cyclobutylmethyl)-4',5'-epoxy-14'-fluorospiro[1,3-dioxolane-2,6'-morphinan]-3'-ol The above obtained amide ester (step b) was heated with lithium aluminum hydride (1 g) in tetrahydrofuran (50 ml) at reflux for 3½ hours. After cooling the reaction mixture, the excess reducing agent was decomposed by adding ethyl acetate, then water, and then dilute potassium bicarbonate solution until the pH was ca. 8.5. The inorganic salts were filtered off, and the filter cake washed with hot tetrahydrofuran. The filtrate was evaporated to dryness and the residue washed thoroughly with water and air dried. Recrystallization from methanol yielded 700 mg of the title compound whch melted at 173°–174°.

From the filtrate, an additional 600 mg of the product was obtained by column chromatography on silica gel.

Mass spectrum: Calcd. $C_{23}H_{28}NO_4F$, 401; found, 401.

EXAMPLE 5

17-(Cyclobutylmethyl)-4,5-epoxy-14-fluoro-3-hydroxymorphinan-6-one

17'-(Cyclobutylmethyl)-4',5'-epoxy-14'-fluorospiro-[1,3-dioxolane-2,6'-morphinan]-3'-ol (1.3 g) was added to a solution of oxalic acid (4.8 g in 80 ml of water) and heated at reflux for a period of 18 hours. The reaction mixture was cooled, and then basified with ammonia to pH 9.2. The precipitated solids were collected by filtration, washed with water, and air dried. The crude material melted at 100° with slight softening and sintering at 93°. The infrared spectrum indicated the presence of a carbonyl group (C=O), 1700 $cm^{-1}$.

EXAMPLE 6

17-(Cyclobutylmethyl)-4,5-epoxy-14-fluoro-morphinan-3,6-diol (α-isomer)

17-(Cyclobutylmethyl)-4,5-epoxy-14-fluoro-3-hydroxymorphinan-6-one (1.1 g) was dissolved in tetrahydrofuran (50 ml) and dried over molecular sieves. This dried solution was then added to a solution of lithium tri(tertiarybutoxy)aluminum hydride (7.5 g in 50 ml THF) and stirred for three hours. Excess reducing agent was decomposed by cautious addition of water followed by sodium carbonate to pH 8.2. The aqueous tetrahydrofuran was filtered off, and the filter cake washed with tetrahydrofuran to leach out the adhering product. The organic solvent was removed by evaporation, the residue dissolved in chloroform, and the chloroform solution washed with water and filtered through a fluted filter. Evaporation of the chloroform yielded 800 mg of a solid which was recrystallized from ethanol to give the title product, m.p. 236°–239°.

EXAMPLE 7

17-Methyl-14-fluoro-3-hydroxy-4,5-epoxymorphinan-6-one a. To a stirred suspension of 4',5'-epoxyspiro[1,3-dioxolane-2,6'-morphinan]-3',14'-diol (16.5 g; 0.05 mole) in 400 ml of methylene chloride, triethylamine (20 ml) was added, ethyl chloroformate (10 ml; 0.1 mole) was added (exotherm) and the mixture stirred for 1 hour. The reaction mixture was then washed cautiously with 600 ml of ice-cold 3% aqueous hydrochloric acid, ice-cold water, saturated sodium bicarbonate, and then water. The organic phase was finally dried over molecular sieves.

The methylene chloride solution was filtered and evaporated to dryness to yield a gum which was purified by column chromatography using 400 g of silica gel, and a mixture of 95 chloroform and 5 ethanol as eluant. Yield of purified 3,17-carboethoxy derivative, 9.2 g.

b. The purified urethane described above (step a) was dissolved in 200 ml of methylene chloride, and this solution added to a cooled solution of diethylaminosulfurtrifluoride (8 ml in 200 ml methylene chloride; −70° C.). The solution was stirred for two hours at that temperature, and then the temperature was allowed to rise gradually to room temperature. After the reaction mixture stood overnight, it was then poured onto 400 g of ice and 400 ml of saturated sodium bicarbonate. The mixture was stirred well, the separated methylene chloride layer was washed several times with water and evaporated. The residue was recrystallized from ethanol to yield 6.3 g of a product which melted at 188°–190°.

Mass Spectrum: Calcd. $C_{24}H_{27}NO_8F$, 477; found, 477.

c. To a solution of 5.4 g of the 14-fluoroketal described above (step b) in 150 ml of tetrahydrofuran, lithium aluminum hydride (2.1 g) was added; the mixture was refluxed for three hours, and then cooled. Ethyl acetate (30 ml) was then added, followed by aqueous saturated potassium bicarbonate, and then a few pieces of dry ice were added to bring the pH to 9.0. An additional 500 ml of tetrahydrofuran was then added, the mixture stirred, and the insoluble organic salts were removed by filtration. The filtrate was then evaporated to dryness. The residue was triturated with water to yield 3.7 g of a granular solid, m.p. 93°–98°.

Mass Spec: Calcd. $C_{19}H_{22}NO_4F$, 347; found, 347.

d. Deketalization Procedure

The above-described ketal (step c) was mixed with 60 ml of 1 N HCl, refluxed overnight (16 hours approx.), and then cooled. Non-basic organic material was removed by ether extraction. The aqueous acidic solution was then basified with ammonia to pH 9.2. The liberated compound was extracted with chloroform, washed, and the chloroform evaporated. Residue was then recrystallized from ethanol to yield 1.5 g of material that melted at 215°–217°.

Mass Spec.: Calcd. $C_{17}H_{18}NO_3F$, 303; found, 303.

All of the compounds in Table I can be prepared by these procedures.

TABLE I

| Example No. | $R_1$ | $R_2$ | $R_3$ | m.p. (°C.) |
|---|---|---|---|---|
| 1 | $CH_3$ | ketal (1,3-dioxolane) | ▷—$CH_2$ | 163–164° |
| 2 | $CH_3$ | =O | ▷—$CH_2$ | 99–102° |
| 3 | H | =O | ▷—$CH_2$ | 188–190° |
| 4 | H | ketal (1,3-dioxolane) | □—$CH_2$ | 173–174° |
| 5 | H | =O | □—$CH_2$ | 100° Sinters at 93° |
| 6 | H | HO (α-isomer) | □—$CH_2$ | 236–239° |
| 7 | H | =O | $CH_3$ | 215–217° |
| 8 | $CH_3$ | ketal (1,3-dioxolane) | □—$CH_2$ | 193–194° |
| 9 | $CH_3$ | =O | □—$CH_2$ | 84–86° |
| 10 | $CH_3$ | ketal (1,3-dioxolane) | $CH_3$ | 174–176° |
| 11 | $CH_3$ | =O | $CH_3$ | 182–184° |

TABLE I-continued

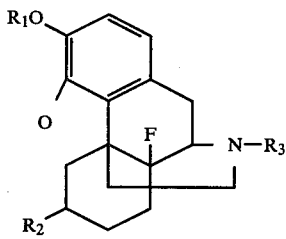

| Example No. | $R_1$ | $R_2$ | $R_3$ | m.p. (°C.) |
|---|---|---|---|---|
| 12 | $\underset{\underset{CH_3C}{\|}}{O}$ | =O | ▷—CH$_2$ | |
| 13 | $\underset{\underset{CH_3(CH_2)_3C}{\|}}{O}$ | =O | ▷—CH$_2$ | |
| 14 | H | =O | $(CH_2)_4CH_3$ | |
| 15 | H | =O | $CH_2CH=CH_2$ | |
| 16 | H | =O | $CH_2CH=C(CH_3)_2$ | |

Utility

The compounds of this invention can be administered orally at doses of about 0.01–100 mg/kg or preferably 0.05–25 mg/kg or more preferably 0.10–10 mg/kg. The compounds also can be given parenterally. The useful daily human oral dose is expected to be in the range of 1–200 mg. A typical dosage form could be capsules or a compressed tablet containing 1 to 25 mg active ingredient administered 1–4 times daily.

Analgesic Testing Procedure

A standard procedure for detecting and comparing the analgesic activity of compounds in this series for which there is good correlation with human efficacy is the standard phenylquinone writhing test modified from Siegmund, et al., *Proc. Soc. Exp. Biol. Med.*, 95, 729 (1957). A test compound suspended in 1% Methocel ® was given orally to fasted (17–21 hours) female white mice, 5–20 animals per double blind test. Aqueous phenylquinone (0.1% phenyl-p-benzoquinone) was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947).

Narcotic Testing Procedure

Narcotic analgesics which have only agonist activity produce in mice an erection and arching of the tail (90° or more) which is referable to spinal cord stimulation. This Straub tail reaction is not produced by other analgesics, including the narcotic antagonists.

The method used was modified from Shemano, I., and Wendel, H., *Tox. Appl. Pharm.*, 6, 334–9 (1964). $CF_1S$ female mice (18–21 g), 10–20 mice per dose, were incubated with log scaled doses of analgesic in 1% aqueous methylcellulose. A positive Straub tail response was recorded if a tail was erected 90° or more for 5 seconds at any time within 24 minutes after dosing. A quantal Straub tail $ED_{50}$ was calculated by the moving average method [Thompson, W. R., *Bact. Rev.*, 11, 115–145 (1947)].

Narcotic Antagonist Testing Procedure

Known narcotic antagonists such as naloxone and nalorphine prevent the induction of Straub tail in mice by a highly addicting agonist such as morphine [H. Blumberg, H. B. Dayton and P. S. Wolf, *The Pharmacologist*, 10, 189 (1968)]. This property is the basis of a mouse test for narcotic antagonists.

Female $CF_1S$ mice (fasted 17–21 hrs.), 5 per dose, were injected orally or subcutaneously with test drug at 0.67, 2, 6, 18, 54 and 162 mg/kg or other appropriate doses in 0.20 ml 1% Methocel ® per mouse. Five minutes later, 30 mg/kg of morphine sulfate in 0.20 ml 1% Methocel ® per mouse was given intraperitoneally. Starting ten minutes later, the mice were observed continuously for 5 minutes for evidence of Straub tail. Prevention of Straub tail during this observation period was taken as indication of narcotic antagonist ability.

The data are in Table II. Most of the compounds were analgetic in the mouse antiphenylquinone test system and only a few caused Straub tail. Most also were antagonists in the mouse anti-Straub tail test.

TABLE II

| | EFFECT $ED_{50}$ | | | |
|---|---|---|---|---|
| Example No. | Anti-Straub Tail (s.c.) | (Oral) | Anti-PQW (Oral) | Straub-tail (Oral) |
| 1 | 1.7 | —* | 42 | >135 |
| 2 | 0.33 | — | >135 | >135 |
| 3 | 0.01 | 0.09 | >135 | >135 |
| 6 | 0.41 | — | 30.4 | >135 |
| 7 | >81 | — | 2.4 | 18.7 |
| 8 | >135 | — | 11.1 | >135 |
| 9 | 6.0 | — | 27.6 | >135 |
| 10 | >135 | — | 5.0 | >135 |
| 11 | >135 | — | 6.3 | 45 |

*An entry of "—" means not tested by the oral route.

Anorexia Testing Procedures

Female $CF_1$ mice, which had been fasted for 17 to 21 hours, were dosed orally with the test compound at 4, 12, 36, 108 or 324 mg/kg (five mice at each dose). One-half hour later, each mouse was transferred to an individual compartment (13.3 cm × 12.7 cm × 12.7 cm) with a 0.64 cm × 0.64 cm wire mesh floor. Inside each compartment was a black bar (13 cm × 1.2 cm × 1.2 cm) in the top of which were ten spot depressions (0.8 cm diameter). Each depression contained 0.05 ml of 50% sweetened condensed milk. Thirty minutes after the mice were transferred into the compartments, the number of milk spots each mouse has consumed was counted. Fractions of spots consumed also were estimated and counted. The five mice tested at each dose could consume a maximum of fifty spots; an anorexigenic effect was considered to be obtained when fifteen or fewer spots were consumed. The doses at which an anorexigenic effect was obtained for the tested compounds are presented in Table III.

TABLE III

| Anorexigenic Effect | |
|---|---|
| Example No. | Effective Dose (mg/kg) |
| 3 | 22.6 |

TABLE III-continued

| Example No. | Anorexigenic Effect Effective Dose (mg/kg) |
|---|---|
| Naloxone | 4.8 |

Dosage Formulations

The compounds of the present invention have utility as analgesics, narcotic antagonists and/or anorexigenic agents.

The well-known narcotic antagonists naloxone and naltrexone have been described to be useful for treating many conditions. Naloxone and naltrexone as well as other narcotic antagonists have been described (U.S. Pat. No. 4,267,182) to be useful in the therapy of shock. Naloxone has been observed to protect against and reverse cardiovascular shock caused by hemorrhage, trauma and sepsis. Naloxone alters sexual activity in a direction that may be therapeutic (increased performance in impotent males). Since it has been noted that naloxone lowers prolactin levels in men, it may be useful in treating gynecological disorders including infertility and menstrual and menopausal disorders. Naloxone has been reported to reverse the neurological deficits caused by anoxia, hemorrhage, aging (manifested by decreased cognition, alertness, etc.) and other pathological processes and may speed the healing of such processes once they have begun. Naloxone may prevent the onset of these processes. Certain mental health disorders (hallucinations of schizophrenia) have improved following naloxone administration, particularly when neuroleptics are also administered. Duration of alcohol intoxication has been shortened by naloxone. Chronic alcoholic patients may benefit from naloxone treatment. Opiate addicts remain abstinent on chronic oral naltrexone therapy. Since naloxone reverses the respiratory depression caused by narcotic overdosage, it and related compounds may have usefulness in the treatment of other types of endogenous and exogenous respiratory dysfunction. Naloxone has local anesthetic efficacy and has been used as an antipruritic as described in U.S. Pat. No. 4,181,726. Naloxone and naltrexone are useful in the treatment of irritable bowel syndrome and naloxone has been suggested to be useful as an antinauseant. It is expected that the compounds of the present invention that have narcotic antagonist activity will also be useful for treating many if not all of these same conditions, since they, like naltrexone, share certain chemical and pharmacological properties with naloxone. An example of this is the anorectic effect described above.

Administration and formulation of the compounds will depend to some extent upon their ultimate use.

Analgesic and narcotic antagonistic agents of this invention can be administered to treat pain or alleviate the effect of narcotic agents by any means that produces contact of the active agent with the agent's site of action in the body of a mammal. The anorexigenic agents should be administered orally. The compounds can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 0.05 to 25 and preferably 0.10 to 10 milligrams per kilogram per day given in divided doses 1 to 4 times a day or in sustained release form is effective to obtain desired results.

Dosage forms (compositions) suitable for internal administration contain from about 0.1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film-coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 25 milligrams of powdered active ingredient, 200 milligrams of lactose, 24 milligrams of talc, and 6 milligrams magnesium stearate.

Capsules

A mixture of active ingredient in soybean oil is prepared and injected by means of a positive displacement pump into gelatin to form soft gelatin capsules containing 25 milligrams of the active ingredient. The capsules are washed in petroleum ether and dried.

Tablets

A large number of tablets are prepared by conventional procedures so that the dosage unit is 25 milligrams of active ingredient, 6 milligrams of magnesium stearate, 70 milligrams of microcrystalline cellulose, 11 milligrams of cornstarch and 300 milligrams of lactose. Appropriate coatings may be applied to increase palatability or delay absorption.

Injectable

A parenteral composition suitable for administration by injection is prepared by stirring 2.0% by weight of active ingredient in 10% by volume propylene glycol and water. The solution is sterilized by filtration.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 gram of sorbitol solution, U.S.P., and 0.025 milliliter of vanillin.

What is claimed is:

1. A compound having the formula:

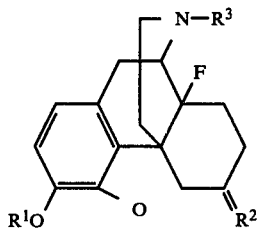

wherein
$R^1$ is —H, —CH$_3$ or

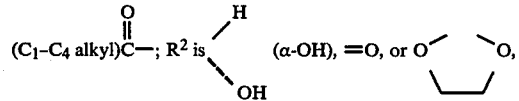

or (O—C$_1$ to C$_6$ alkyl)$_2$; and
$R^3$ is C$_1$-C$_5$ alkyl,

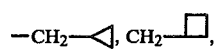

allyl or 3,3-dimethylallyl;
or a pharmaceutically suitable salt thereof.

2. A compound of claim 1 wherein $R^1$ is —H, —CH$_3$ or acetyl.

3. A compound of claim 1 wherein $R^3$ is

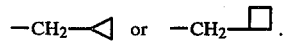

4. A compound of claim 1 wherein $R^1$ is —H, —CH$_3$ or acetyl and $R^3$ is

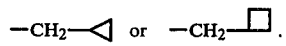

5. The compound of claim 1 wherein $R^1$ is —H; $R^2$ is =O; and $R^3$ is

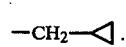

6. The compound of claim 1 wherein $R^1$ is —H;

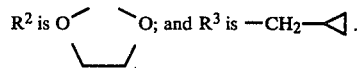

7. A pharmaceutical composition consisting essentially of a suitable pharmaceutical carrier and an effective analgesic amount or antagonist amount or anorexigenic amount of a compound of claim 1, or claim 2, or claim 3, or claim 4, or claim 5, or claim 6.

8. A method of producing analgesia or narcotic withdrawal or an anorexigenic effect in a mammal comprising administering to a mammal an analgesic effective amount or a narcotic antagonist effective amount or an anorexigenic effective amount of a compound of claim 1, or claim 2, or claim 3, or claim 4, or claim 5, or claim 6.

* * * * *